US 9,744,003 B2

(12) United States Patent
Goodman

(10) Patent No.: US 9,744,003 B2
(45) Date of Patent: Aug. 29, 2017

(54) ORTHODONTIC TORQUING

(76) Inventor: Phillip M. Goodman, Simpsonville, SC (US)

( * ) Notice: Subject to any disclaimer, the term of this patent is extended or adjusted under 35 U.S.C. 154(b) by 702 days.

(21) Appl. No.: 13/638,242

(22) PCT Filed: Mar. 31, 2011

(86) PCT No.: PCT/US2011/000583
§ 371 (c)(1),
(2), (4) Date: Sep. 28, 2012

(87) PCT Pub. No.: WO2011/126550
PCT Pub. Date: Oct. 13, 2011

(65) Prior Publication Data
US 2013/0040259 A1    Feb. 14, 2013

Related U.S. Application Data

(60) Provisional application No. 61/341,388, filed on Mar. 31, 2010.

(51) Int. Cl.
*A61C 3/00* (2006.01)
*A61C 7/04* (2006.01)
*A61C 7/22* (2006.01)

(52) U.S. Cl.
CPC . *A61C 7/04* (2013.01); *A61C 7/22* (2013.01)

(58) Field of Classification Search
CPC ................................ A61C 7/04; A61C 7/22
(Continued)

(56) References Cited

U.S. PATENT DOCUMENTS 3,374,542 A * 3/1968 Moylan, Jr. ................. 433/8
3,755,902 A * 9/1973 Northcutt .................... 433/4
(Continued)

FOREIGN PATENT DOCUMENTS

| EP | 1790309 | 5/2007 |
| FR | 2368932 | 5/1978 |
| GB | 1035863 | 7/1966 |

OTHER PUBLICATIONS

International Search Report and Written Opinion from related PCT application PCT/US2011/000583 dated Oct. 11, 2012, 17 pages.

*Primary Examiner* — Cris L Rodriguez
*Assistant Examiner* — Mirayda A Aponte
(74) *Attorney, Agent, or Firm* — Brooks, Cameron & Huebsch, PLLC

(57) ABSTRACT

Embodiments of the present disclosure are directed to devices and a method for orthodontic torquing. For the various embodiments, a pliers for crimping coils of an orthodontic torquing spring to an arch wire includes: a pair of plier halves, each of the plier halves including a handle, a jaw, and a pivot section, each of the jaws including a crimping face defined by a distal edge having a length in a range of 200 percent to 400 percent of a diameter of the orthodontic spring, a first lateral edge, and a second lateral edge, the edges defined by a radius of curvature in a range of 0.1 millimeters to 0.5 millimeters, a textured surface on at least one of the crimping faces to frictionally engage the coil of the orthodontic spring, and a pivot joint connecting the pivot sections of the pair of plier halves such that the handles can be manipulated to cause the crimping faces of the jaws to move together to crimp a coil of the orthodontic torquing spring to the arch wire.

13 Claims, 5 Drawing Sheets

(58) Field of Classification Search
USPC ............... 433/3, 4, 18, 20–22, 24, 106, 159
See application file for complete search history.

(56) References Cited

U.S. PATENT DOCUMENTS

| | | | |
|---|---|---|---|
| 3,781,993 A * | 1/1974 | Cusato | 433/4 |
| 3,975,823 A | 8/1976 | Sosnay | |
| 4,392,494 A * | 7/1983 | Ashby | 433/4 |
| 5,257,558 A * | 11/1993 | Farzin-Nia et al. | 433/4 |
| 5,328,361 A * | 7/1994 | Ezcurra | 433/4 |
| 5,542,843 A | 8/1996 | Price | |
| 5,588,832 A | 12/1996 | Farzin-Nia | |
| 2005/0097998 A1 | 5/2005 | Herbst et al. | |
| 2005/0186536 A1* | 8/2005 | Zepf | 433/159 |
| 2007/0122763 A1* | 5/2007 | Farzin-Nia | 433/4 |

* cited by examiner

ORTHODONTIC TORQUING

RELATED APPLICATIONS

This application is a National Stage application under 35 U.S.C. 371 of PCT/US2011/000583, filed on Mar. 31, 2011 and published as WO2011/126550 A2 on Oct. 13, 2011, which claims the benefit of U.S. Provisional Application Ser. No. 61/341,388 filed Mar. 31, 2010, the entire contents of which are incorporated herein by reference in its entirety.

FIELD OF DISCLOSURE

Embodiments of the present disclosure are directed to orthodontics, specifically devices for orthodontic torquing.

BACKGROUND

Many orthodontic treatment techniques move teeth in a procedure involving two stages. In the initial stage the forces applied to the crowns of the teeth displace the crown more than the root causing a tipping movement. The latter stage utilizes moments of force which are also applied to the crowns of the teeth in order to upright the roots and place them in a position of proper axial inclination, commensurate with normal function, favorable aesthetics, and stability. This latter stage may be termed the torquing stage.

Lingual root torque is difficult to achieve particularly on the maxillary anterior teeth. One reason for this is that all forces must be applied to the crown, while the center of resistance to moving the roots is located in a remote position along the apical portion of the root surface. This results in a situation of severe mechanical disadvantage.

There are several orthodontic appliances that have been directed at root torquing. Many of the early approaches generally consisted of three basic elements: 1) metal bands which circumferentially encompass the crown of each tooth and are attached to each tooth by cementation; 2) brackets of varying configurations affixed to the metal bands; and 3) base arch wire—usually of a U-shape which fits through slots in each of the brackets. The base arch wire is generally round or rectangular in cross-section. In some applications brackets have been attached directly to the tooth surface by means of bonding. The arch wire may act in an active or passive capacity. In the passive mode, it may act as a track along which the teeth are repositioned. Alternatively, the active mode incorporates deformations into the base arch wire during fabrication of the wire. When an orthodontic professional places the arch wire into position within the bracket slots, these deformations may serve to produce forces and moments which move teeth during orthodontic treatment.

Other attempts at orthodontic torquing have been made using a loop and a pair of legs on substantially the same plane. In this type of approach, each leg terminates in a pair of coil sets, each of the coil sets are helically wound and the outer coil set is closely associated with and fixedly anchored to the arch wire while the other coil-set of each pair is maintained free of the arch wire and in unrestricted movement with respect to the arch wire. The loop engages the labial surface of a tooth and applies force to the tooth.

These past approaches, however, have been ineffective for their purpose. For example, attaching coil sets to an arch wire in the past has involved soldering, slide fitting, and/or force fitting. None of these approaches have exhibited commercial viability and thus the long-felt need to provide orthodontic torquing has gone unmet. Generally, orthodontic professionals cannot solder the coil sets to an arch wire because material limitations cause the coil sets to immediately degrade and crumble when soldered. Similarly, efforts to crimp the coils to an arch wire result in broken coils. Force and/or slide fitting can no longer be practical because modern arch wires do not exhibit the square edges of old wires.

Thus, it is desired to provide an orthodontic torquing system that does not have the ineffectiveness of the above described systems.

SUMMARY

One or more embodiments of the present disclosure include a pliers for crimping coils of an orthodontic torquing spring to an arch wire, an orthodontic torquing spring, and a method of crimping a coil of an orthodontic torquing spring to an arch wire. For the various embodiments, the pliers includes: a pair of plier halves, each of the halves including a handle, a jaw, and a pivot section, each of the jaws including a crimping face defined by a distal edge having a length in a range of 200 percent to 400 percent of a diameter of the orthodontic torquing spring, a first lateral edge, and a second lateral edge, the edges defined by a radius of curvature in a range of 0.1 millimeters to 0.5 millimeters, a textured surface on at least one of the crimping faces to frictionally engage the coil of the orthodontic torquing spring, and a pivot joint connecting the pivot sections of the pair of plier halves such that the handles can be manipulated to cause the crimping faces of the jaws to move together to crimp a coil of the orthodontic torquing spring to the arch wire.

In one or more embodiments, the method includes providing a pliers, including two handles, two jaws, and a pivot section, each of the jaws including a crimping face defined by a distal edge having a length in a range of 200 percent to 400 percent of a diameter of the orthodontic torquing spring, a first lateral edge, and a second lateral edge, the edges defined by a radius of curvature in a range of 0.1 millimeters to 0.5 millimeters, positioning the pliers such that the crimping faces contact substantially opposing sides of a circumference of at least one coil of the orthodontic torquing spring helically encircling a portion of the arch wire, applying a force to at least one of the handles such that the crimping faces move together, and crimping at least one coil of the orthodontic torquing spring to the arch wire.

In one or more embodiments, the orthodontic torquing spring includes: a first spring coil portion, a second spring coil portion, and a loop extending between the first and second spring coil portions, where each of the first spring coil portion, the second spring coil portion, and the loop are formed of a wire having a diameter of 0.330 to 0.356 millimeters.

The above summary of the present disclosure is not intended to describe each disclosed embodiment or every implementation of the present disclosure. The description that follows more particularly exemplifies illustrative embodiments.

BRIEF DESCRIPTION OF THE DRAWINGS

The following drawings illustrate non-limiting embodiments of the present disclosure, wherein.

DETAILED DESCRIPTION

Figure 1:
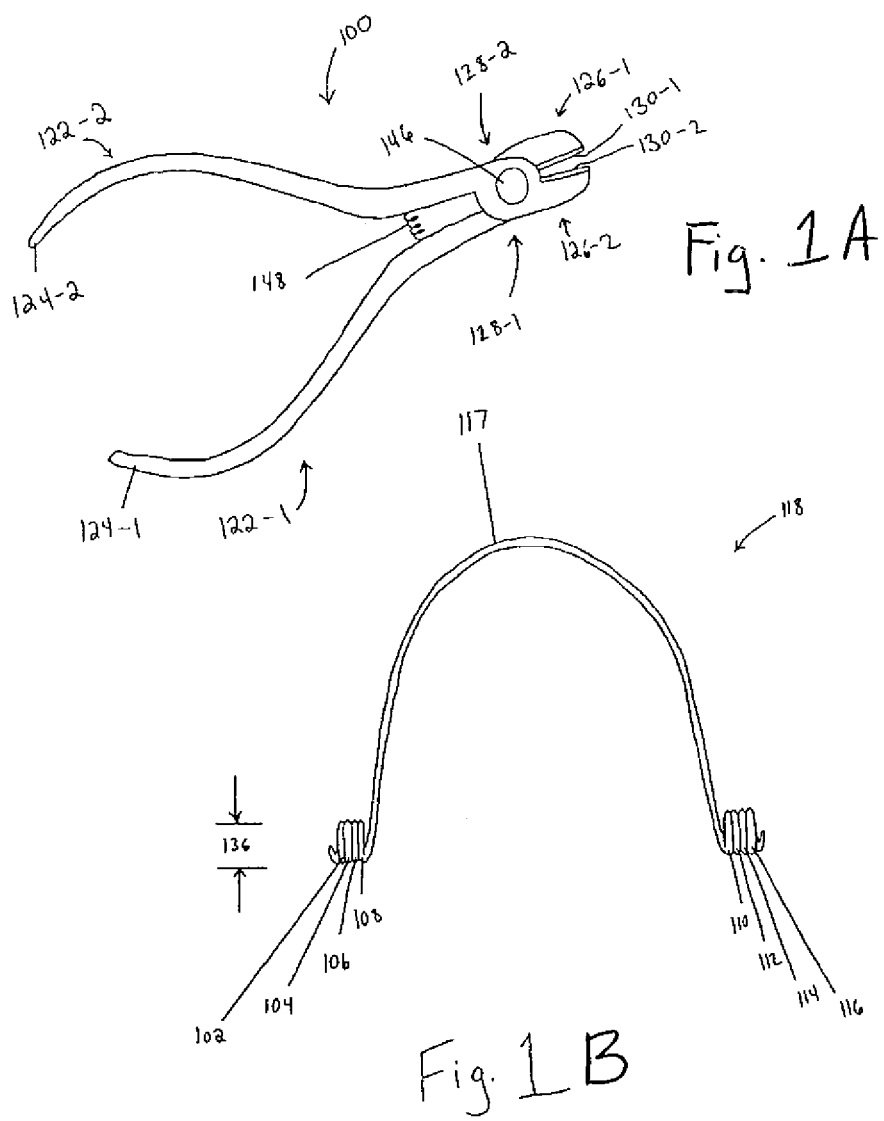
FIGS. 1A and 1B illustrate a pliers for crimping coils of an orthodontic torquing spring (FIG. 1A) and an orthodontic torquing spring (FIG. 1B) according to one or more embodiments of the present disclosure.

In the following detailed description of the present disclosure, reference is made to an accompanying drawing that forms a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, chemical and/or structural changes may be made without departing from the scope of the present disclosure.

The figures herein follow a numbering convention in which the first digit or digits corresponds to the drawing figure number and the remaining digits identify an element in the drawing. Similar elements between different figures may be identified by the use of similar digits. For example, 106 may reference element "06" in FIG. 1, and a similar element may be referenced as 206 in FIG. 2. The proportion and the relative scale of the elements provided in the figures are intended to illustrate various embodiments of the present invention and are not to be used in a limiting sense.

The present disclosure provides embodiments for an orthodontic torquing spring, a pliers for crimping an orthodontic torquing spring to an arch wire, and a method of crimping an orthodontic torquing spring to an arch wire. One or more embodiments according to the present disclosure allow for an orthodontic torquing spring to be crimped onto an arch wire at a desired angle to provide for a desired level of torquing force to a labial surface of a tooth. Further, embodiments of the present disclosure provide a pliers for crimping an orthodontic torquing spring that reduces the chance of unsuccessful or ineffectual affixation of an orthodontic torquing spring to an arch wire. Embodiments of the present disclosure allow for an orthodontic torquing spring that does not require soldering, does not crumble and/or degrade when crimped to an arch wire, and is adapted and manufactured to be crimped to various sizes of arch wire.

Unlike embodiments of the present disclosure, past approaches have been ineffective for their purpose. Some approaches (e.g., those comparable to the system disclosed in U.S. Pat. No. 3,975,823 (Sosnay)) require a torquing spring to be soldered or welded to an arch wire. Upon welding and/or soldering, torquing springs like those disclosed in U.S. Pat. No. 3,975,823 may have a tendency to crumble and/or degrade, rendering the spring useless. Further, past approaches have been designed to be force-fit around an arch wire having a square cross-section and sharp 90 degree edges. Because wired with square edges are more difficult to insert into orthodontic bracket slots, patients experience heightened discomfort as the arch wire exerts more pressure upon their teeth. Thus, the use of square edged wires has been greatly diminished in the orthodontic profession. Without the sharp edges of the older-style arch wire, previous approaches like those disclosed in U.S. Pat. No. 3,975,823 have nothing against which to 'bite' and can exert little to no actual torque. Orthodontic professionals using previous torquing approaches and arch wires without sharp edges are left with the option of soldering, which, as previously discussed, may cause material failure.

Although it may not have been disclosed in the previous approaches (e.g., U.S. Pat. No. 3,975,823) some orthodontic professionals have tried to crimp the springs of previous approaches to arch wires in an effort to avoid the issues surrounding force fitting and soldering. However, these orthodontic professionals have found that springs of previous approaches may also have a tendency to break when crimping force is exerted upon them.

Thus, for many years, the needs of orthodontic professionals to effectively apply torquing force to teeth have gone unmet. This problem may be overcome by the various embodiments of the present disclosure. Indeed, it has been noted that embodiments of the present disclosure have been well-received in the orthodontic community. Orthodontists understand the difficulties associated with solving root position problems, like, for example, those involved with ectopically-positioned, malposed, and/or impacted teeth, among others. Embodiments of the present disclosure are said to solve these problems both easily and efficiently, whereas past approaches have failed.

FIG. 1 illustrates a pliers 100 and an orthodontic torquing spring 118 according to one or more embodiments of the present disclosure. Pliers 100 can include two plier halves 122-1, 122-2, each, for example, including a handle 124-1, 124-2, a jaw 126-1, 126-2, and a pivot section 128-1, 128-2. Each of the jaws can include a crimping face 130-1, 130-2. Materials included in the plier halves 122-1 and 122-2 of pliers 100 include those known to ones skilled in the art, including, for example, steel alloys and/or titanium alloys, among other materials. The two plier halves 122-1, 122-2 can be connected at their respective pivot sections 128-1, 128-2 by a pivot joint 146. The handles 124-1, 124-2 can be manipulated to cause the jaws 126-1, 126-2 to move towards and/or away from each other. For example, movement of the handles 124-1, 124-2 towards each other, can cause plier half 122-1 to pivot, relative to the other plier half 122-2, around pivot joint 146 and the jaws 126-1, 126-2 to move towards each other. Pivot joint 146 can include one or more lubricants (e.g., oil, grease, graphite, and/or other lubricants) to reduce friction, prevent corrosion, improve efficiency and/or reduce wear, among other concerns.

Although not illustrated in FIG. 1, pivot joint 146 can include an adjustable component. Adjustable components will be known to those of ordinary skill in the art, and include, for example, a hexagonal nut, a threaded bolt, a wing nut, and/or a thumb nut, among others. An adjustable component can also include a locking mechanism (e.g., a cotter pin and/or R-clip, among others). An adjustable component can enable tightening and/or loosening of the pivot joint 146, and can further allow for disjoining of plier halves 122-1 and 122-2 to allow, for example, cleaning, relubrication, and/or general maintenance.

Pliers 100 can also include a recoil mechanism 148. If, for example, a user is manipulating an object while manipulating pliers 100, recoil mechanism 148 can exert opposing forces on the interior side of the plier halves 122-1 and 122-2, thereby causing them to pivot at the pivot joint 146, moving handle 124-1 away from handle 124-2, and simultaneously moving jaw 126-1 away from jaw 126-2. Recoil mechanism 148 can include, for example, a compression spring, a leaf spring, and/or a volute spring, among others. Further, recoil mechanism 148 can be adjustable by, for example, choice of spring material, and/or number of coils in spring, among others. Recoil mechanism 148 can allow a user to open (e.g., partially open) the jaws 126-1, 126-2 by easing the force used to squeeze the plier handles 124-1, 124-2 together.

FIG. 1 further illustrates an orthodontic torquing spring 118 according to one or more embodiments of the present disclosure. Orthodontic torquing spring 118 can include, for example, a loop portion 117 terminating at one end with a number of coils 102, 104, 106, 108, and at the other end with a number of coils 110, 112, 114, 116, each having an outer diameter 136. As discussed below, with reference to FIGS. 2, 3, and 4, the coils (e.g., coils 102, 104, 106, 108, 110, 112, 114, 116) can include an interior diameter of sufficient size to accept an orthodontic arch wire passing therethrough (e.g., an arch wire having a cross-section in a range of 0.406 millimeters×0.559 millimeters to 0.483 millimeters. 0.635 millimeters). As those skilled in the art will appreciate, orthodontic torquing spring 118 can include a number of materials. Materials used in orthodontic torquing spring 118 can include, for example, heat treated spring steel, stainless steel, titanium alloys, Elgiloy (an alloy including cobalt, chromium, and nickel), and/or nitonol, among other materials. Orthodontic torquing spring 118 can be crimped to arch wires made from, for example, copper titanium, nickel titanium, and/or titanium molybdenum alloy, among other metals and/or metal alloys.

Figure 2:
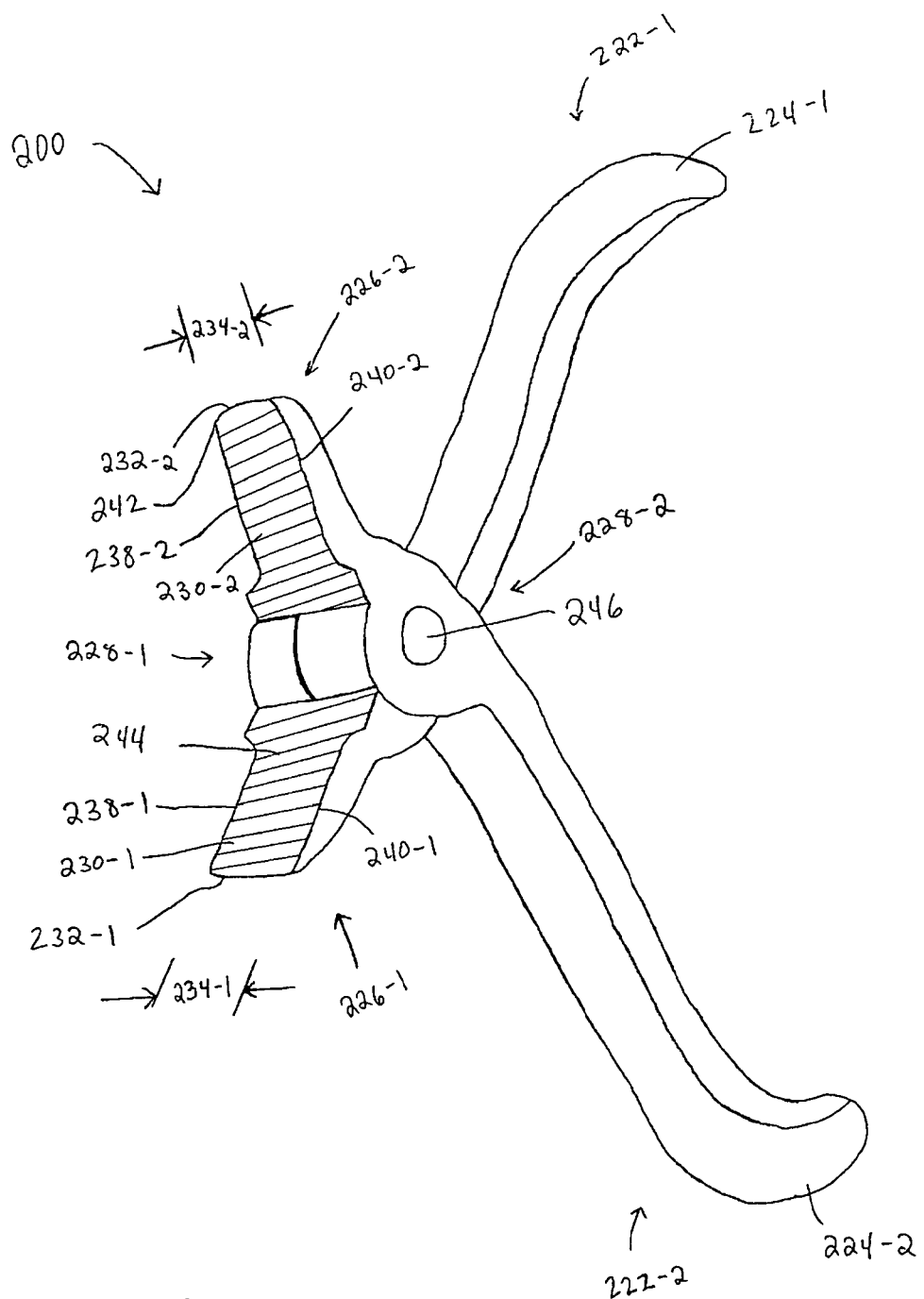
FIG. 2 illustrates a pliers for crimping coils of an orthodontic torquing spring according to one or more embodiments of the present disclosure.

FIG. 2 illustrates pliers 200 according to one or more embodiments of the present disclosure. Pliers 200 can include two plier halves 222-1, 222-2, each, for example, including handle 224-1, 224-2, jaw 226-1, 226-2, and pivot section 228-1, 228-2. Each of the jaws can include crimping face 230-1, 230-2. The two plier halves 222-1, 222-2 can be connected at their respective pivot sections 228-1, 228-2 by pivot joint 246. The handles 224-1, 224-2 can be manipulated to cause jaws 226-1, 226-2 to move towards and/or away from each other. For example, movement of handles 224-1, 224-2 towards each other, can cause plier half 222-1 to pivot, relative to the other plier half 222-2, around pivot joint 246 and jaws 226-1, 226-2 to move towards each other. Pivot joint 246 can include one or more lubricants as discussed above with reference to FIG. 1.

Pliers 200 includes two crimping faces 230-1, 230-2. Crimping face 230-1 and/or 230-2 can include a textured surface 244 to frictionally engage a coil of the orthodontic torquing spring 118. Textured surface 244 can include material that is of a greater hardness than the remainder of pliers 200 to, for example, aid in a tight crimp. Materials used in and/or on the textured surface 244 can include, for example, calcium carbide, silicon carbide, tungsten carbide, and/or cementite, among others. Also, textured surface 244 can include a number of different textures. Textures on the textured surface 244 can include the surface being machined/and or a coating applied thereto. Machining textures can include knurled, serrated, grooved, crosshatched, and/or etched, among other textures.

Referring to the jaws 226-1 and 226-2 of pliers 200, each jaw can include a distal edge and two lateral edges. For example, jaw 226-1 includes distal edge 232-1, a first lateral edge 238-1, and a second lateral edge 240-1; jaw 226-2 includes distal edge 232-2, first lateral edge 238-2, and second lateral edge 240-2. It will be appreciated by those skilled in the art that pliers 200 is adapted to crimp a coil of an orthodontic torquing spring (e.g., coil 102 of spring 118) and not cut and/or otherwise cleave the coil. To this end, for example, jaw edges of pliers 200 can be rounded to a radius of curvature 242. Radius of curvature 242 can include a radius of curvature in a range of 0.1 to 0.5 millimeters. Although not illustrated in FIG. 2, jaw edges of pliers 200 can also be, for example, beveled.

Distal edge 232-1 can have a length 234-1 in a range of 200 percent to 400 percent of a diameter 136 of an orthodontic torquing spring 118. Distal edge 232-2 can have a length 234-2 in a range of 200 percent to 400 percent of a diameter 136 of an orthodontic torquing spring 118. Lateral edges 238-1, 238-2, 240-1, and/or 240-2 can have lengths in a range of 900 percent to 1300 percent of the diameter 136 of an orthodontic torquing spring 118. Those skilled in the art will appreciate that shorter lateral edges yield more crimping force per unit of force applied to the handles 224-1 and 224-2.

Figure 3A:
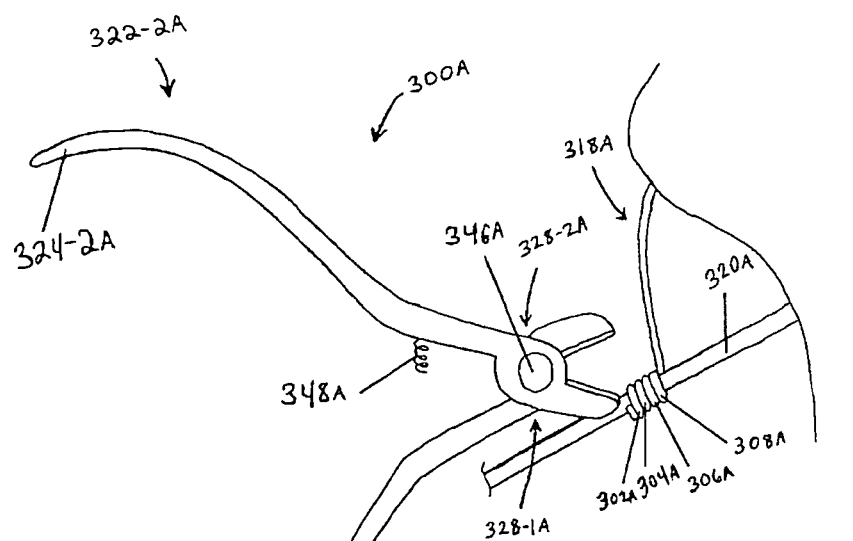
FIG. 3A illustrates a pliers for crimping coils of an orthodontic torquing spring approaching coils of an orthodontic torquing spring according to one or more embodiments of the present disclosure.
Figure 3B:
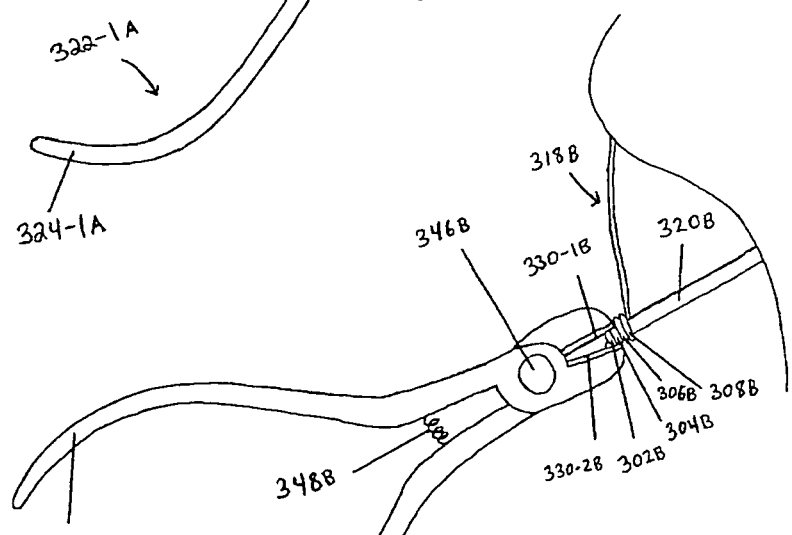
FIG. 3B illustrates a pliers crimping coils of an orthodontic torquing spring according to one or more embodiments of the present disclosure.

FIGS. 3A and 3B illustrate a pliers 300A, 300B, and an orthodontic torquing spring 318A, 318B with an orthodontic arch wire 320A, 320B passing through a number coils 302A, 304A, 306A, 308A, 302B, 304B, 306B, 308B of the spring 318A, 318B. Pliers 300A, 300B can include two plier halves 322-1A, 322-2A, 322-1B, 322-2B each, for example, including a handle 324-1A, 324-2A, 324-1B, 324-2B, a jaw 326-1A, 326-2A, 326-1B, 326-2B and a pivot section 328-1A, 328-2A, 328-1B, 328-2B. Each of the jaws can include a crimping face 330-1A, 330-2A, 330-1B, 330-2B. The two plier halves 322-1A, 322-2A, 322-1B, 322-2B can be connected at their respective pivot sections 328-1A, 328-2A, 328-1B, 328-2B by a pivot joint 346A, 346B. The handles 324-1A, 324-2A, 324-1B, 324-2B can be manipulated to cause the jaws 326-1A, 326-2A, 326-1B, 326-2B to move towards and/or away from each other. For example, movement of the handles 324-1A, 324-2A, 324-1B, 324-2B towards each other, can cause a plier half 322-1A, 322-1B to pivot, relative to the other plier half 322-2A, 322-2B around pivot joint 346A, 346B and the jaws 326-1A, 326-2A, 326-1B, 326-2B to move towards each other. In a manner analogous to that previously discussed with reference to FIG. 1, pliers 300A, 300B includes a recoil component 348A, 348B.

FIG. 3B illustrates the pliers embodied in FIG. 3A crimping coils 302B and 304B of orthodontic torquing spring 318B. Pliers 300B can be positioned such that the distal edge 232-1, 232-2 of the jaws 326-1A, 326-2A, 326-1B, 326-2B is substantially parallel to the longitudinal axis of the orthodontic torquing spring 318A, 318B while pliers 300B is crimping. However, positioning of pliers 300B during crimping is not limited to parallel orientation, rather, pliers 300B can be positioned perpendicular to the longitudinal axis of the orthodontic torquing spring 318A, 318B, and/or at another angle between parallel and perpendicular.

Figure 4:
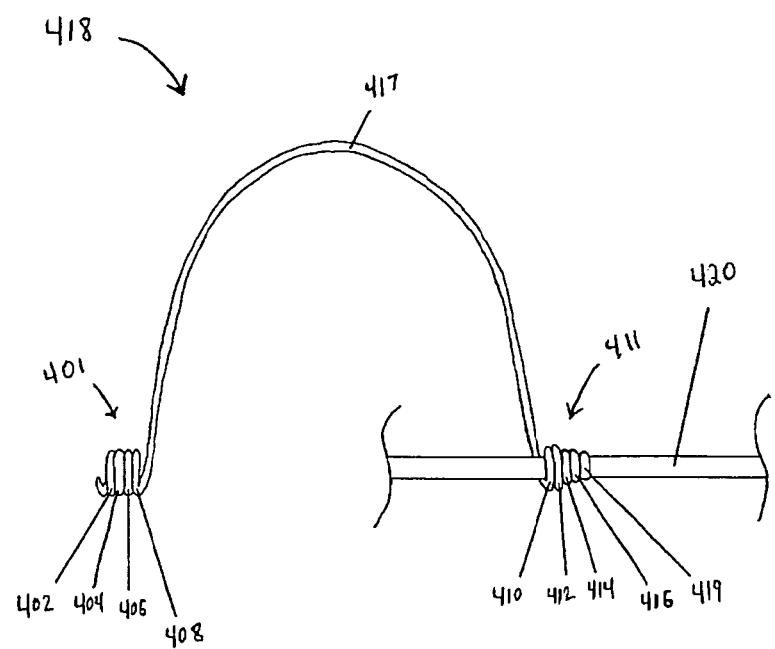
FIG. 4 illustrates an orthodontic torquing spring that has had one coil set crimped to an arch wire according to one or more embodiments of the present disclosure.

FIG. 4 illustrates an orthodontic torquing spring 418 crimped to an arch wire 420. Orthodontic torquing spring 418 can include a loop portion 417, a first spring coil portion 401 having a number of coils 402, 404, 406, 408, and a second spring coil portion having a number of coils 410, 412, 414, 416, 419. As shown in FIG. 4, three (3) coils of orthodontic torquing spring 418 can be crimped to an arch wire 420. However, embodiments of the present disclosure are not limited to a particular number of coils being crimped. Those skilled in the art will appreciate that crimping in a range of 50 percent to 75 percent of the coils of the orthodontic torquing spring 418 can maintain orthodontically-acceptable torquing levels. As shown in FIG. 4, first spring coil portion 401 and second spring coil portion 411 do not share an equal number of active coils. Embodiments of the present disclosure are not limited to an unequal number of active coils between spring portions. Rather, it may be advantageous in various embodiments to maintain an equal number of active coils between spring coil portion 401 and spring coil portion 411. One or more embodiments according to the present disclosure may include an orthodontic torquing spring including a pitch in a range of 0.055 to 0.066 millimeters. Those skilled in the art will appreciate that orthodontic torquing spring 418 can be crimped to arch wire 420 at a desired angle with respect to a labial surface of a tooth. Once crimped, orthodontic torquing spring 418 can apply a force for torquing in a range of 50 to 150 grams of force (0.49 Newtons to 1.47 Newtons of force) on the tooth in question.

Figure 5:
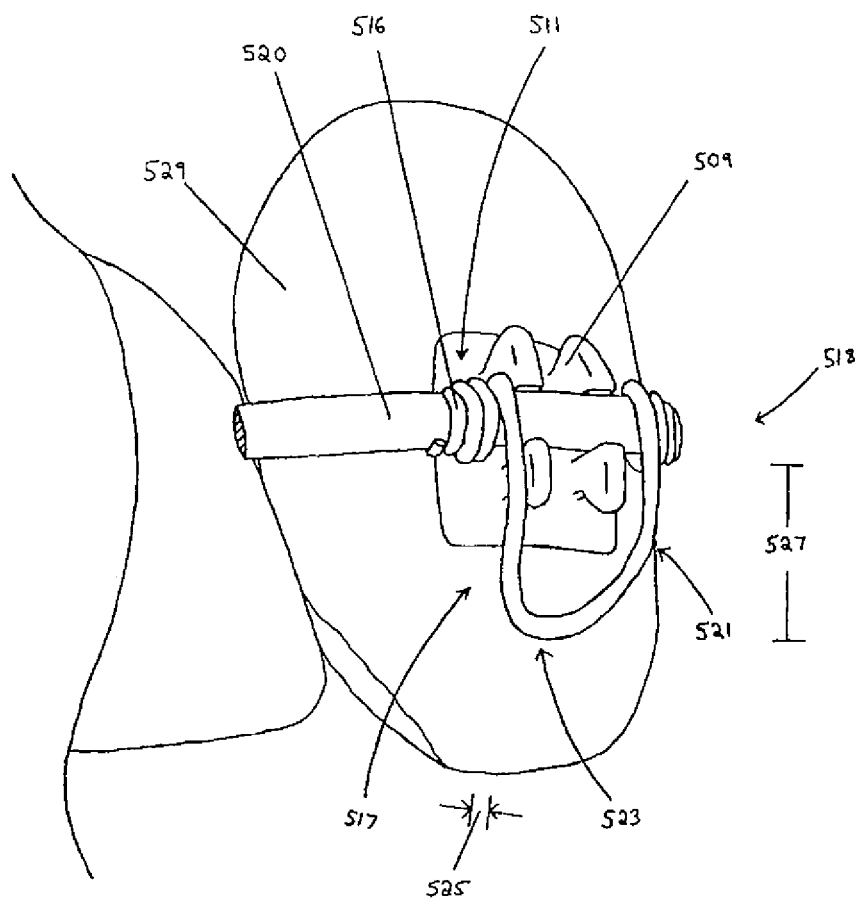
FIG. 5 illustrates an orthodontic torquing spring crimped to an arch wire torquing a tooth.

FIG. 5 illustrates orthodontic torquing spring 518 with coil 516 of second spring coil portion 511 crimped to arch wire 520. A ligature (e.g., a rubber band) to secure arch wire 520 to an orthodontic bracket 509 is not illustrated in FIG. 5 in order to illustrate orthodontic spring 518 more clearly. Orthodontic torquing spring 518 is shown in FIG. 5 engaging a labial surface of tooth 529 and applying torquing force thereto. As illustrated in FIG. 5, orthodontic torquing spring 518 can be made from a wire having a diameter 525. Diameter 525 can range, for example, from 0.330 to 0.356 millimeters. Loop portion 517 extends from second spring coil portion 511 and engages tooth 529 at the apex 523 of loop portion 517. Loop portion 517 can have a length 527 from a coil (e.g., coil 516) to the apex 523 of the loop 517. Length 527 can extend, for example, in a range of 3.5 millimeters to 4.9 millimeters away from coil 516. As illustrated in FIG. 5, loop portion 517 can include a curve 521 perpendicular to a longitudinal axis of a spring coil portion (e.g., second spring coil portion 511). Embodiments of the present disclosure having curve 521 can, among other things, allow the loop portion 517 to bypass orthodontic bracket 509 on the labial side of a tooth 529 and engage the labial surface of tooth 529 at the apex 523 of loop portion 517.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A pliers for crimping coils of an orthodontic torquing spring to an arch wire comprising:
   a pair of plier halves, each of the plier halves including a handle, a jaw, and a pivot section, each of the jaws including a substantially rectangular shaped crimping face defined by a distal edge having a length in a range of 200 percent to 400 percent of a diameter of the orthodontic torquing spring, a first lateral edge, and a second lateral edge that extend substantially perpendicularly from the distal edge, where each of the distal edge, the first lateral edge and the second lateral edge have a radius of curvature in a range of 0.1 millimeters to 0.5 millimeters;
   a textured surface on at least one of the substantially rectangular shaped crimping faces to frictionally engage the coil of the orthodontic torquing spring; and
   a pivot joint connecting the pivot sections of the pair of plier halves such that the handles can be manipulated to cause the substantially rectangular shaped crimping faces of the jaws to move together to crimp a coil of the orthodontic torquing spring to the arch wire.

2. The pliers of claim 1, where the first lateral edge has a length in a range of 900 percent to 1300 percent of the diameter of the orthodontic torquing spring.

3. The pliers of claim 1, where the second lateral edge has a length in a range of 900 percent to 1300 percent of the diameter of the orthodontic torquing spring.

4. The pliers of claim 1, where the pivot joint is selectively adjustable by a hexagonal nut.

5. The pliers of claim 1, where the textured surface is one of calcium carbide, silicon carbide, tungsten carbide, and cementite.

6. The pliers of claim 1, where the textured surface includes the surface being knurled.

7. The pliers of claim 1, where the textured surface includes the surface being serrated.

8. The pliers of claim 1, further comprising a recoil component disposed between the handles of the plier halves.

9. A method of crimping a coil of an orthodontic torquing spring to an arch wire comprising:
   providing a pliers, including two handles, two jaws, and a pivot section, each of the jaws including a substantially rectangular shaped crimping face defined by a distal edge having a length in a range of 200 percent to 400 percent of a diameter of the orthodontic torquing spring, a first lateral edge, and a second lateral edge that extend substantially perpendicularly from the distal edge, where each of the distal edge, the first lateral edge and the second lateral edge have a radius of curvature in a range of 0.1 millimeters to 0.5 millimeters;
   positioning the pliers such that the substantially rectangular shaped crimping faces contact substantially opposing sides of a circumference of at least one coil of the orthodontic torquing spring helically encircling a portion of the arch wire;
   applying a force to at least one of the handles such that the substantially rectangular shaped crimping faces move together; and
   crimping at least one coil of the orthodontic torquing spring to the arch wire.

10. The method of claim 9, where positioning the pliers includes positioning the distal edge of the substantially rectangular shaped crimping face substantially parallel to a longitudinal axis of the orthodontic torquing spring.

11. The method of claim 9, where positioning the pliers includes positioning the distal edge of the substantially rectangular shaped crimping face substantially perpendicular to a longitudinal axis of the orthodontic torquing spring.

12. The method of claim 9, where the method includes positioning the pliers such that a textured surface on the substantially rectangular shaped crimping face frictionally engages a surface of the orthodontic torquing spring.

13. The method of claim 9, where the method includes crimping a number of coils in a range of 50 percent to 75 percent of the coils of the orthodontic torquing spring.

* * * * *